United States Patent
Hering et al.

(10) Patent No.: US 8,088,627 B2
(45) Date of Patent: Jan. 3, 2012

(54) ON-LINE GAS CHROMATOGRAPHIC ANALYSIS OF AIRBORNE PARTICLES

(75) Inventors: Susanne V. Hering, Berkeley, CA (US); Allen H. Goldstein, Orinda, CA (US)

(73) Assignees: Aerosol Dynamics, Inc., Berkeley, CA (US); The Regents of the University of California, Oakland, CA (US)

( * ) Notice: Subject to any disclaimer, the term of this patent is extended or adjusted under 35 U.S.C. 154(b) by 975 days.

(21) Appl. No.: 11/008,851

(22) Filed: Dec. 10, 2004

(65) Prior Publication Data
US 2005/0244980 A1   Nov. 3, 2005

Related U.S. Application Data

(60) Provisional application No. 60/528,729, filed on Dec. 10, 2003.

(51) Int. Cl.
*G01N 30/06* (2006.01)
(52) U.S. Cl. ............. 436/161; 422/70; 73/23.41; 95/82; 96/101
(58) Field of Classification Search ............. 422/70; 436/161; 73/23.35–23.42; 95/82–89; 96/101–107
See application file for complete search history.

(56) References Cited

U.S. PATENT DOCUMENTS

| | | | | |
|---|---|---|---|---|
| 5,177,995 A | * | 1/1993 | Risch et al. | 73/23.41 |
| 5,191,211 A | * | 3/1993 | Gorman, Jr. | 250/282 |
| 5,970,803 A | * | 10/1999 | Staples et al. | 73/863.12 |
| 5,983,732 A | * | 11/1999 | Hering et al. | 73/863.22 |

OTHER PUBLICATIONS http://www.thefreedictionary.com/impaction.*
http://www.thefreedictionary.com/impingement.*
http://www.thefreedictionary.com/aerosol.*

* cited by examiner

*Primary Examiner* — Jan Ludlow
(74) *Attorney, Agent, or Firm* — Vierra Magen Marcus & DeNiro LLP

(57) ABSTRACT

A method and apparatus for the in-situ, chemical analysis of an aerosol. The method may include the steps of: collecting an aerosol; thermally desorbing the aerosol into a carrier gas to provide desorbed aerosol material; transporting the desorbed aerosol material onto the head of a gas chromatography column; analyzing the aerosol material using a gas chromatograph, and quantizing the aerosol material as it evolves from the gas chromatography column. The apparatus includes a collection and thermal desorption cell, a gas chromatograph including a gas chromatography column, heated transport lines coupling the cell and the column; and a quantization detector for aerosol material evolving from the gas chromatography column.

16 Claims, 13 Drawing Sheets

Sampling/Analysis Mode

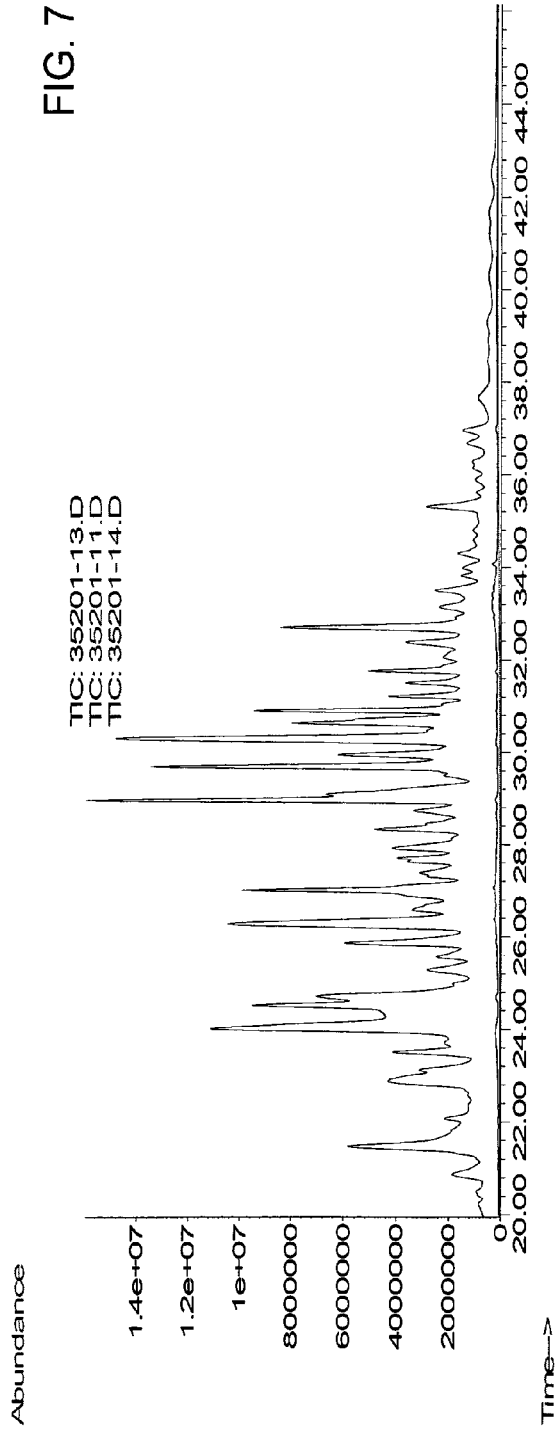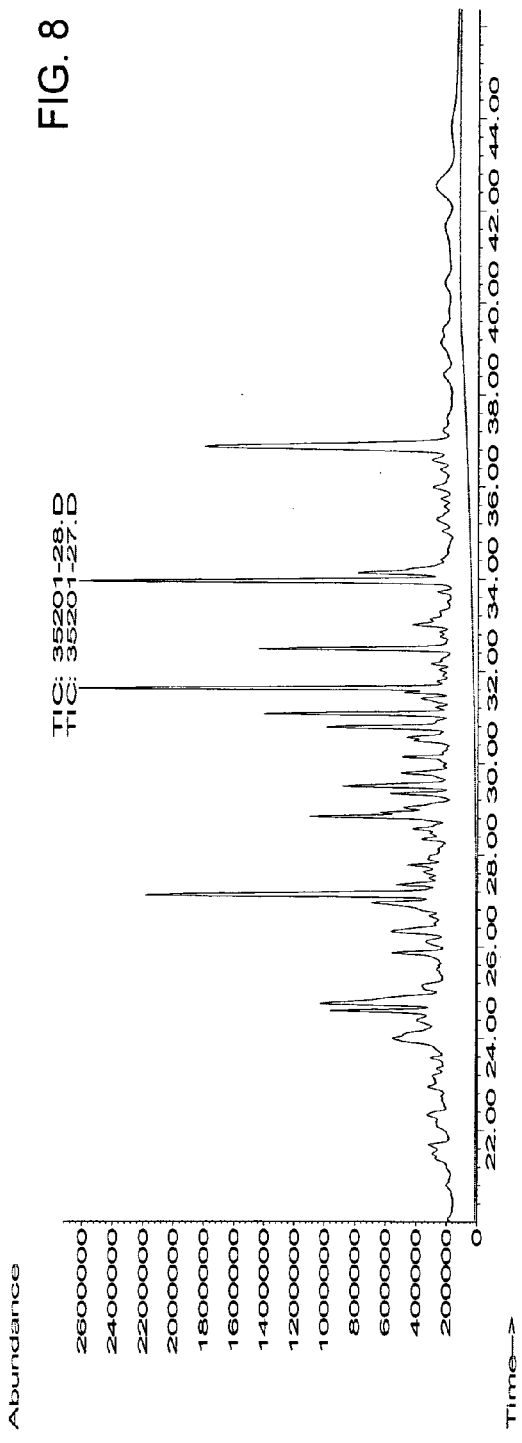

ON-LINE GAS CHROMATOGRAPHIC ANALYSIS OF AIRBORNE PARTICLES

CLAIM OF PRIORITY

This application claims the benefit of U.S. Provisional Application No. 60/528,729, "On-line Gas Chromatographic Analysis of Airborne Particles," filed on Dec. 10, 2003, which is incorporated herein by reference.

This invention was made with government support under Grant No.: DE-FG02-03ER83825 from the US Department of Energy. The government has certain rights in the invention.

BACKGROUND OF THE INVENTION

1. Field of the Invention

This invention pertains to the automated, semi-continuous identification of specific organic compounds at the molecular level, and the determination of the concentration of these particle-bound organic compounds in airborne particles.

2. Description of the Related Art

Organic matter is a major constituent of airborne particulate matter (PM), and may comprise 20-50% of the mass of those particles with diameters smaller than 2.5 μm ($PM_{2.5}$). (See, for example, Chow, J. C., Watson, J. G., Lowenthal, D. H., Solomon, P. A., Magliano, K. L., Ziman, S. D., Richards, L. W., 1993. PM10 and PM2.5 compositions in California's San Joaquin Valley. *Aerosol Science and Technology* 18: 105-128; Schauer J. J. and Cass G. R. (2000) Source apportionment of wintertime gas-phase and particle phase air pollutants using organic compounds as tracers, *Environ. Sci. Technol.* 34: 1821-1832; Kim, B. M., Teffera, S., Zeldin, M. D., 2000. Characterization of PM2.5 and PM10 in the South Coast air basin of southern California: Part 1n—spatial variation. *J. Air and Waste Management Assoc.* 50: 2034-2044; Christoforou, C. S., Salmon, L. G., Hannigan, M. P., Solomon, P. A., Cass, G. R., 2000. Trends in fine particle concentration and chemical composition in southern California. *J. Air and Waste Management Assoc.* 50: 43-53; NARSTO. (2003). Particulate Matter Sciences for Policy Makers, A NARSTO Assessment, Chapter 6.

The chemical composition of organic matter is complex and largely not understood. Many hundreds of organic compounds have been identified through chromatography and mass spectrometry techniques including alkanes, substituted phenols, alkanals, sugar derivatives, aromatic polycyclic hydrocarbons, mono- and di-carboxylic acids.

While the compounds which have been identified comprise only a fraction of the total organic mass, those that are quantified serve as valuable tracers for sources. For example, hopanes, which are remnants of the biological material from which petroleum originated, serve as a unique tracer for fossil fuel combustion. Levoglucosan is a product of the breakdown of cellulose, and is a unique tracer for wood combustion. Biogenic alkanes are distinguished from fossil-derived alkanes through a carbon preference number that reflects the predominance of odd-carbon number alkanes in plant waxes. These differences in organic compound composition have been used to determine the relative contribution of various source types to primary ambient organic matter (See, for example, Schauer J. J. and Cass G. R. (2000) Source apportionment of wintertime gas-phase and particle phase air pollutants using organic compounds as tracers, *Environ. Sci. Technol.* 34: 1821-1832; Fraser M. P., Kleeman, M. J., Schauer, J. J., Cass, G. R. (2000) Modeling the Atmospheric Concentrations of Individual Gas-Phase and Particle-Phase Organic Compounds, *Environ. Sci. Technol.*, 34: 1302-1312; Fine, P. M., Cass G. R., Simoneit, B. R. T. (2001) Chemical characterization of fine particle emissions from fireplace combustion of woods grown in the northeastern United States, *Environ. Sci. Technol.* 35: 2665-2675; Yue, Z. and Fraser, M. P. (2003a). Characterization of non-polar organic fine particulate matter in Houstion, Tex. Submitted for publication; Yue, Z. and Fraser, M. P. (2003b). Polar organic compounds measured in Fine Particulate matter during TexAQS 2000. Submitted for publication).

A substantial limitation in the use of organic marker compounds for source identification is the difficulty of the analyses. The identification and quantification of organic matter at the compound level involves integrated sample collection by filtration or impaction with subsequent extraction and analysis by liquid or gas chromatography. Generally large samples are required, and analyses are time-consuming and expensive. These methods have provided valuable insight and guidance in the understanding of airborne organic matter, but are limited by their poor time resolution, intensity of manual efforts, and cost.

Over the last decade, several types of particle beam mass spectrometry methods have emerged for the study of ambient particles, including two methods that are now available commercially (Noble C. A. and Prather K. A. (1996) Real time measurement of correlated size and composition profiles of individual atmospheric aerosol particles, *Environ. Sci. Technol.* 30: 2667-2680. Jayne, J. T., Leard D. C., Zhang X-F. Davidovits P., Smith K. A., Kolb, C. E., Worsnop D. R. (2000) Development of an aerosol mass spectrometer fro size and composition analysis of submicron particles, *Aerosol Sci. Technol.* 33: 49-70). These instruments provide a wealth of real-time data on aerosols and on single particle composition. Yet all face considerable challenges in identifying and quantifying the complex mix of organic compounds found in ambient aerosols. The deconvolution of mass spectra from multiple organic compounds remains a daunting challenge.

Particle-beam mass spectrometers are fast and automated, but do not provide the necessary compound separation for quantitative assay of organic compounds at the molecular level. Filter measurements, with laboratory extraction, chromatographic separation and mass spectrometric analyses provide identification and quantification at the molecular level, but are labor intensive, costly and slow to yield results.

Hence, a high throughput system which provides separation of organic compounds prior to their identification and quantification by a mass spectrometric method, would be highly valuable.

SUMMARY OF THE INVENTION

The present invention, roughly described, pertains to automated, semi-continuous identification at the molecular level of specific organic compounds in airborne particles In one aspect, the invention is a method for the in-situ, chemical analysis of an aerosol. The method may include the steps of: collecting an aerosol; thermally desorbing the aerosol into a carrier gas to provide desorbed aerosol material; transporting the desorbed aerosol material onto the head of a gas chromatography column; analyzing the aerosol material using a gas chromatograph, and quantizing the aerosol material as it evolves from the gas chromatography column. The step of quantizing is advantageously performed by using a mass spectrometer or flame ionization detector, or both in parallel.

In a further aspect, the invention is an in-situ, aerosol chemical analysis device. The device includes a collection and thermal desorption cell, a gas chromatograph including a gas chromatography column, heated transport lines coupling the cell and the column; and a quantization detector for aerosol material evolving from the gas chromatography column. These and other objects and advantages of the present invention will appear more clearly from the following description in which the preferred embodiment of the invention has been set forth in conjunction with the drawings.

BRIEF DESCRIPTION OF THE DRAWINGS

FIG. 7 is a chromatogram of wood smoke sample analyzed directly from CTD cell via thermal desorption, a system blank and a repeat analysis of the collection tube that had already been thermally desorbed.

FIG. 8 is a chromatograms of atmospheric aerosol sample analyzed directly from CTD cell via thermal desorption GC/MS (TIC:35201-28D, upper trace) with comparison to the chromatogram for a system blank (TIC:35201-27.D, lower trace).

FIGS. 9A and 9C show the observed mass spectrum, and FIGS. 9B and 9D shows the library match and identification for each compound respectively

DETAILED DESCRIPTION

The invention provides a method and apparatus for the analysis of organic compounds in airborne particles. In one embodiment, the invention includes a collection and thermal desorption cell that is interfaced directly to a gas chromatograph. The collection and thermal desorption (CTD) cell collects airborne particles as small as 0.08 µm in diameter via impaction. Its collection efficiency is enhanced through humidification of the airstream prior to collection. Compounds of interest in the collected particles are transferred from the CTD cell directly to the head of the gas chromatograph column through thermal desorption at temperatures as high as 350° C. Compounds are focused onto the head of the gas chromatography column by maintaining the column temperature of 50° C. or less. After compound transfer the cell is isolated from the column by means of a valve. Compounds are separated on the chromatographic column using standard methodology, and detected by a mass spectrometer or flame ionization detector, or both. The method is semi-continuous, consisting of sample collection, sample transfer to the separation column, and chromatographic analysis. The method may be automated, allowing for simultaneous collection and analysis, separated by brief periods for sample transfer. Cycle time is approximately one hour.

Figure 1A:
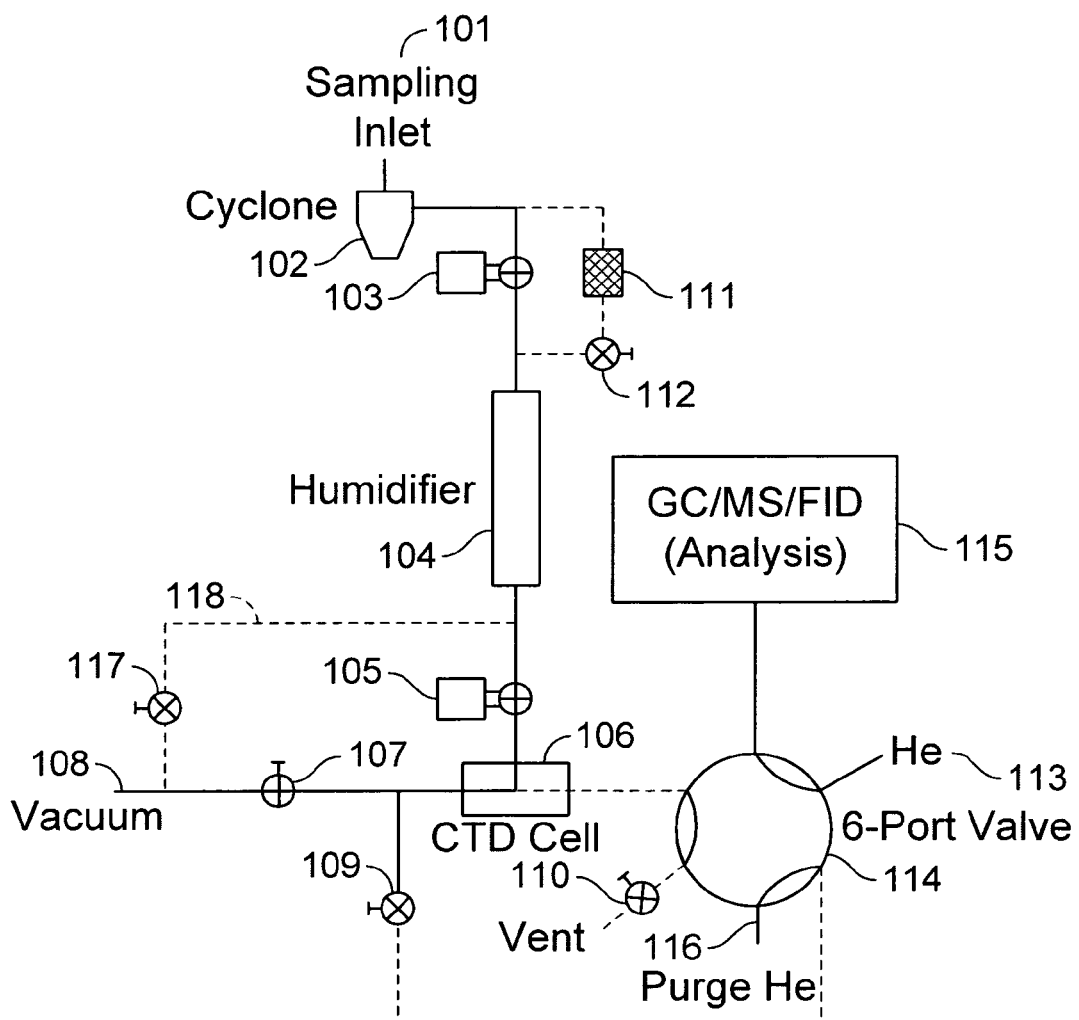
FIG. 1A is a schematic of the instrument showing the collection and thermal desorption (CTD) cell and the gas chromatograph with mass spectrometry and/or flame ionization detection (GC/MS/FID) operating in sampling and analysis mode.
Figure 1B:
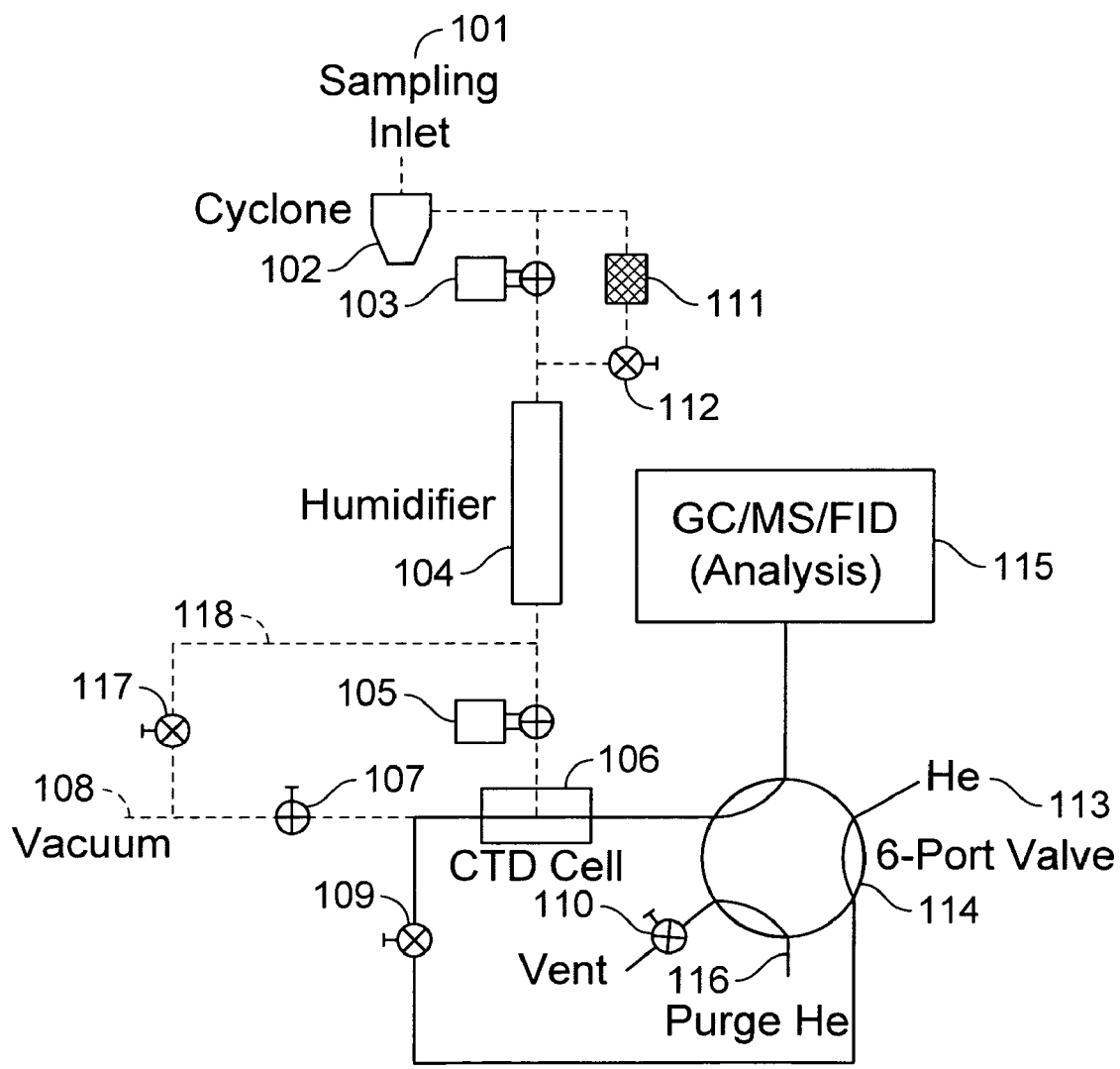
FIG. 1B illustrates the device of FIG. 1A operating in thermal desorption mode.

FIGS. 1A and 1B show a configuration of the in-line aerosol gas chromatograph mass spectrometry system. Each Figure illustrates a different mode of operation used to provide an automated, in-situ measurement system for organic marker compounds in airborne particles. The apparatus of FIGS. 1A and 1B generally consists of a particle collection and thermal desorption (CTD) cell 106 which is interfaced to a gas chromatograph mass spectrometer (GC/MS) 115 with an optional flame ionization detector (FID). The system has two modes of operation: (1) ambient sampling with concurrent GC/MS analysis, (illustrated in FIG. 1A) and (2) thermal desorption and sample injection (illustrated in FIG. 1B). For ambient aerosol sampling the sample collection and concurrent GC/MS analysis takes approximately 50 minutes. The thermal desorption mode is operational only during the time required to desorb and inject the sample into the head of the GC/MS column. This step takes approximately 10 minutes, giving an overall cycle time of one hour.

In one aspect, the modes may be automated to run continuously using a computer to control the various valves and temperatures. In one embodiment, the apparatus may consist of an inlet 101; a $PM_{2.5}$ precut cyclone 102 for particle size selection; a humidifier 104 to reduce particle bounce; an isolation ball valve 105; an integrated collection and thermal desorption (CTD) cell 106, and the GC/MS 115, with its associated transport lines and valves (108, 109, 110, 113, 114, 116, 117, and 118). The cyclone 102 provides a $PM_{2.5}$ precut that excludes particles above 2.5 µm in aerodynamic diameter. Cyclones are commonly used to exclude particles with aerodynamic diameters greater than 2.5 µm from sampling systems, and have the advantage that they do not require oil or grease to particles prevent particle bounce and re-entrainment, thus eliminating a potential source of contamination. The humidifier 104 is used to increase the relative humidity of the sample air stream to a value of 65% or higher. This reduces the bounce of solid particles within the impaction region of the CTD by adding a thin coating of water to the sampled particles. The humidifier may be a Nafion-based system that consists of one or more water semi-permeable Nafion tubes enclosed in a water jacket (PermaPure, Toms River, N.J.). The CTD cell 106 collects the humidified particles by impaction, and then desorbs the collected sample through heating. A ball valve 105 immediately above the CTD cell is open during sampling and closed during the thermal desorption step. The GC/MS provides analysis of the sample. As is generally well known, a gas chromatograph includes a column, oven and detector. A sample being analyzed is introduced onto the head of the chromatographic column. The sample is transported through the column by the flow of inert, gaseous mobile phase. An upstream particle filter 111 may be switched in line automatically by closing ball valve 103 and opening valve 112 to provide a measure of the background signal when no aerosol is sampled. System automation is handled through switching of the various valves, and programmed temperature control.

Figure 1C:
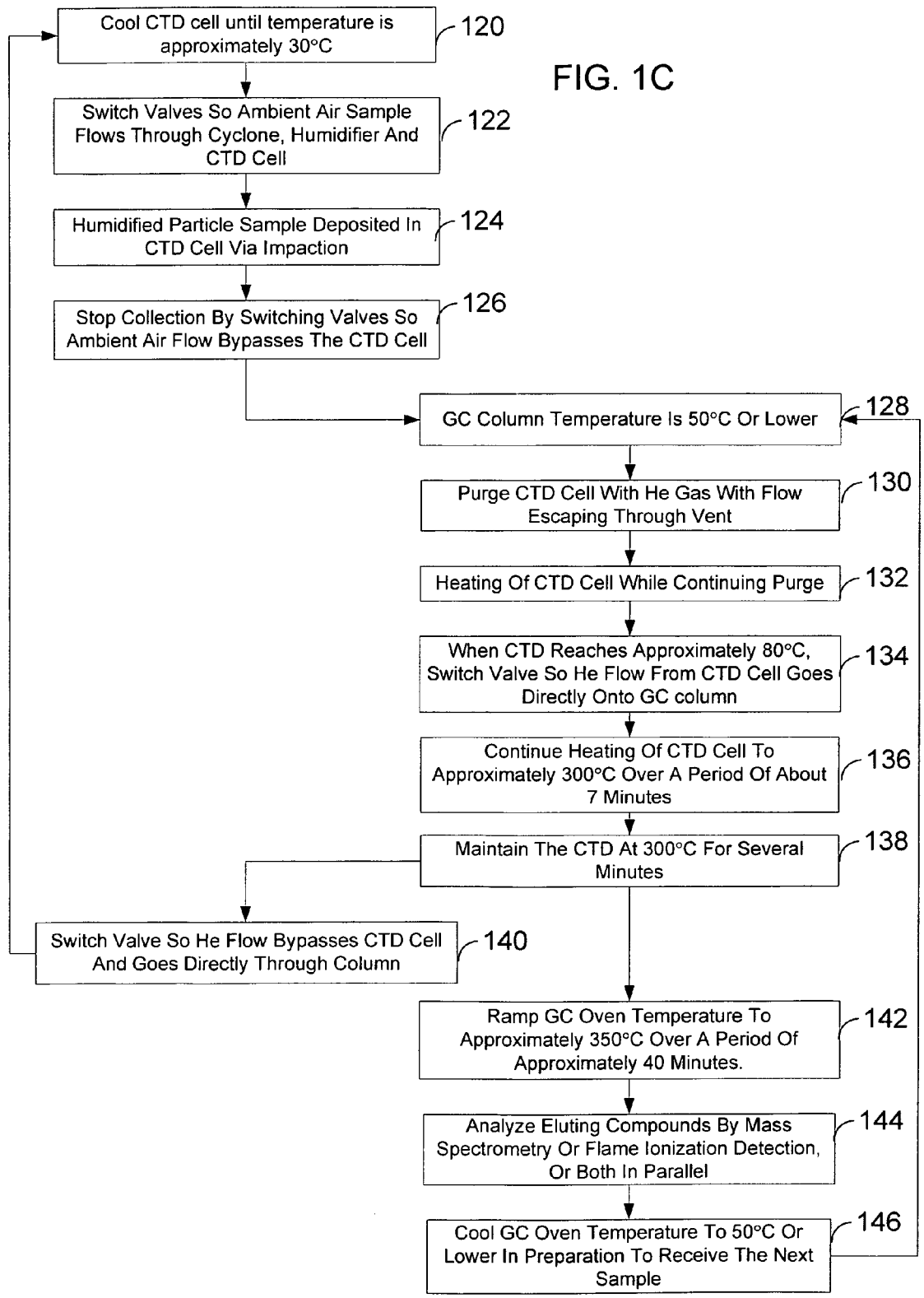
FIG. 1C is a flowchart illustrating the method of the present invention.

FIG. 1C illustrates the method of the present invention. At step 120, the CTD is cooled to a temperature of 30° C. for sample acquisition. At step 122, valves are switched so the air so ambient air sample flows through cyclone, humidifier and CTD cell. During sampling and analysis, either an aerosol or particle free sample stream is directed into the CTD cell concurrent with the GC/MS analysis of the immediately preceding aerosol sample. For aerosol collection, aerosol ball valves 103 and 105 are open, as is valve 107 leading to vacuum 108. The six-port valve 114 is configured to direct Helium (He) gas flow from line 113 into the GC/MS 115, thus permitting sample analysis to proceed. The purge He 116 and vent are isolated from the CTD cell by closing valves 109 and 110. For the measurement of dynamic blanks, defined as the signal for particle-free sampling, valve 103 is closed while valve 112 is open to divert the sample flow through a filter; but is otherwise the same as for aerosol sampling. As a result, at step 124, a humidified particle sample is deposited in the CTD via impaction.

Next, at step 126, collection is stopped by closing valves 105 and 107. The sample flow may be directed around the cell through bypass line 118 by opening valve 117. At some point prior to thermal desorption, at step 128, the GC column temperature is lowered to 50° C. or less. At step 130, the CTD cell is purges with He Gas. Valves 109 and 110 are open to provide a He purge of the cell. The temperature of the cell is slowly increased by means of a heater (not shown) at step 132. Material that desorbs from the cell at low temperature, below approximately 80° C., is mostly water, and is vented through valve 110. After the initial heating, at step 134, the six-port valve 114 is switched so that the He carrier gas is directed through the cell and into the GC/MS. At step 136, the CTD 106 is heated further to approximately 300° C. to desorb the organic compounds in the collected sample. The transfer lines between the CTD and GC column and the 6-port valve 114 are heated to 250-300° C. During step 138, the GC column is held at a temperature of 50° C. or lower, thus trapping the desorbed material at the head of the column. At the end of the desorption step 140, the system returns to the sampling analysis configuration, allowing the GC/MS analysis and the collection of the next sample to proceed.

During analysis, the GC temperature is ramped to approximately 350° C. over a period of approximately 40 minutes at step 142. Next, the compounds are analyzed at step 144 by Mass Spectrometry, Flame Ionization detection, or both in parallel. Finally, the GC oven temperature is cooled at step 146 in preparation for the next sample.

The CTD cell is used to collect particles in a manner amenable to direct thermal desorption onto the GC column. Various configurations of the CTC cell are illustrated in FIGS. 1D-1H.

Figure 1D:
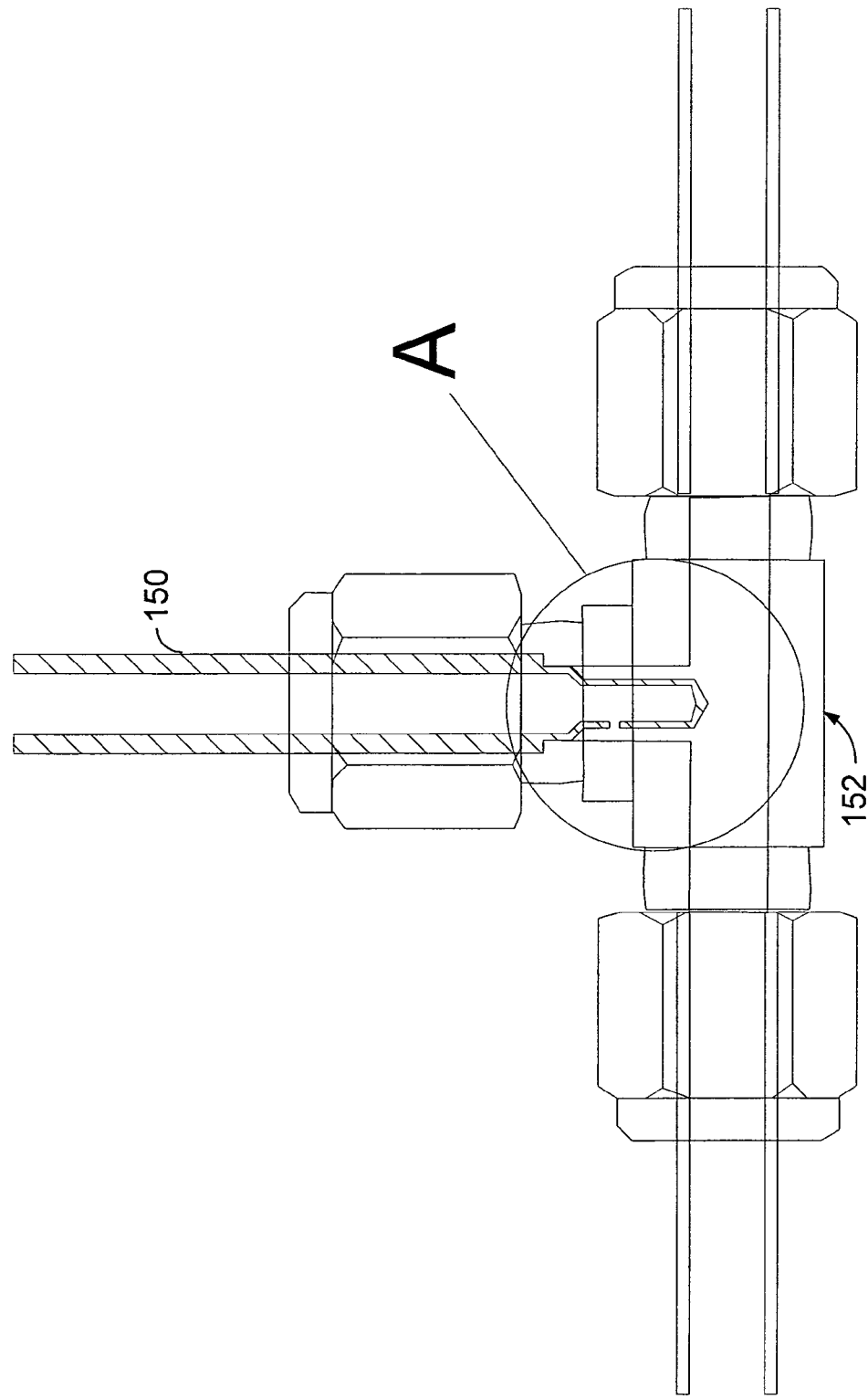
FIG. 1D is an enlarged cut-away view of the CTD illustrated in FIGS. 1A and 1B.
Figure 1E:
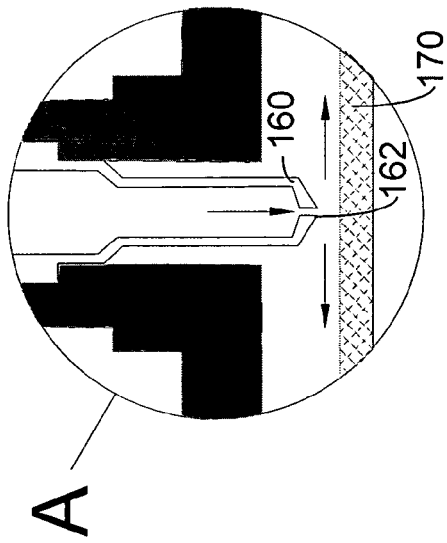
FIG. 1E is an enlarged view of section A of FIG. 1D of a first embodiment of the CTD shown in FIG. 1C.
Figure 1H:
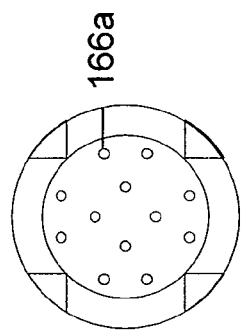
FIG. 1H is a view along line B-B in FIG. 1G.
Figure 1G:
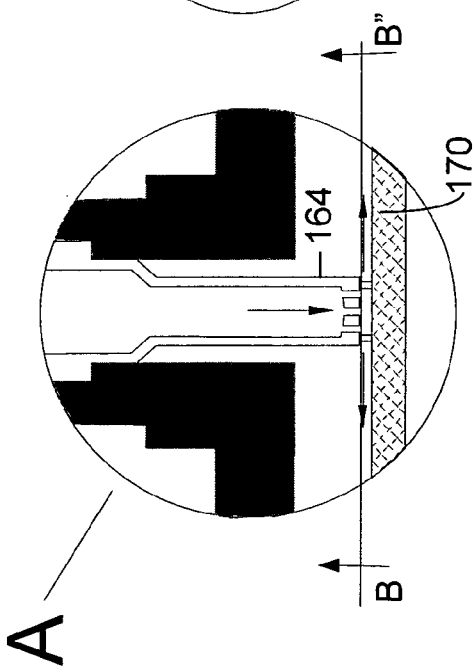
FIG. 1G is an enlarged view of section A of FIG. 1D of a second embodiment of the CTD shown in FIG. 1D.
Figure 1F:
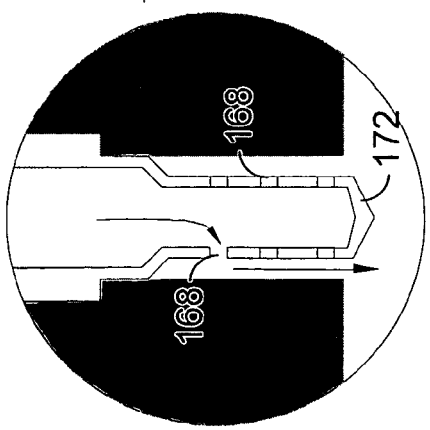
FIG. 1F is an enlarged view of section A of FIG. 1D of a third embodiment of the CTD shown in FIG. 1C.

Three geometries have been tested. All three consist of an orifice tube 150 mounted within a ¼ inch Swagelok tee 152, as shown in FIG. 1D. The tee 152 and orifice tubes 150 are made of 316 stainless steel and are chemically passivated. Chemical passivation may be done by Silcosteel coatings such as are available from Restek Corporation (Bellefonte, Pa.), or Inertium treatment as provided by Advanced Material Components Express (St. College, Pa.) In the first configuration, illustrated in FIG. 1E, the orifice tube 160 has a single orifice 162 with a diameter of 0.37 mm, as shown in FIG. 1E. The flow is 1 L/min, and impinges onto a glass substrate 170 held within the tee. This configuration was used for the testing illustrated with respect to FIGS. 7-10 below. In the second configuration, Illustrated in FIGS. 1G and 1H there are 10 nozzles 166a at the bottom of the orifice tube 164, each with a diameter of 0.28 mm. This is shown in FIGS. 1G and 1H. This multijet configuration operates at a flow rate of 7 L/min, and was used for in conjunction with the reports illustrated in FIGS. 11 and 12 below. A third configuration illustrated in FIG. 1F uses 9 orifices 168 with a diameter of 0.34 mm drilled through the sides of the orifice tube, 172 as shown in FIG. 1F. These are arranged in three rows of three orifices each. Within each row the orifices are equally spaced around the diameter. Between rows the jets are offset by 45° from the neighboring row, such that the exiting airflows do not interfere with each other. In this configuration the jets impinge on the sidewalls of the tee. This configuration was also tested with the fully automated system. With the third configuration the flow of the He carrier gas during the thermal desorption step was directed through the orifice tube as well as through the side arm of the tee.

Experimental Results

The CTD Cell collection efficiency for airborne particles was measured using monodisperse aerosol generated by nebulization and mobility selected by means of a high-flow differential mobility analyzer. Upstream and downstream particle number concentrations were obtained using a pair of TSI 3760 condensation particle counters (CPCs). The downstream counter is operated at low pressure, with a bypass flow to account for the difference in impactor and CPC flow rates. An auxiliary magnehelic installed in the pressure balance line was used to ensure that the instrument was not flooded during pump down. To confirm the particle counting efficiency, measurements were made using a "bypass" orifice with a straight path to the low-pressure CPC. Simple ball valves directed the flow either through the CTD cell or through the bypass orifice. With flow through the bypass orifice the count rate of the two CPCs was directly proportional to the operating pressure, indicating equal counting efficiencies over the 50 to 800 nm size range tested. With flow through the CTD cell relative counts were used to calculate the collection efficiency of the cell.

Figure 2:
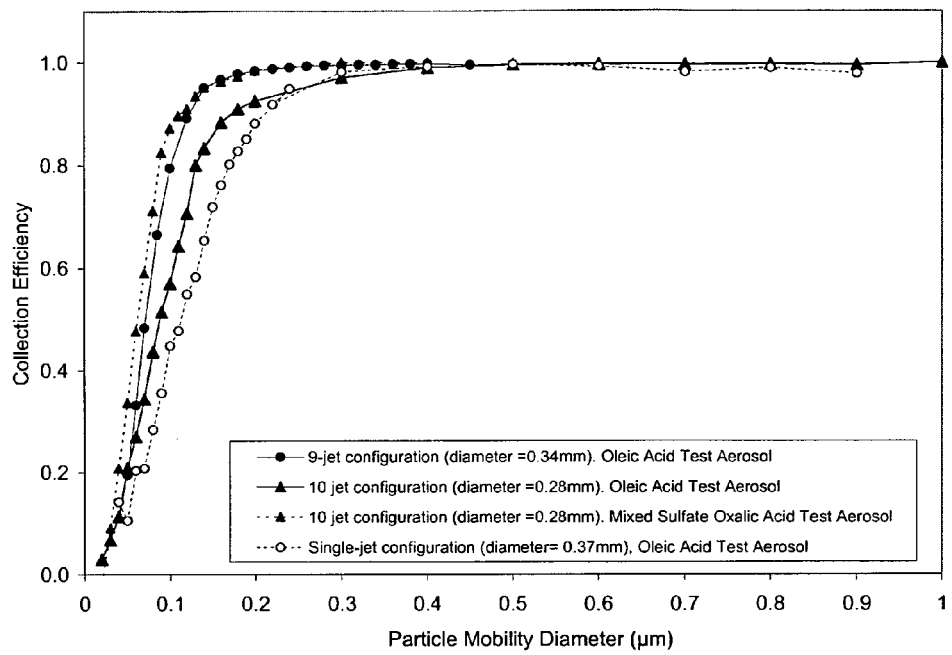
FIG. 2 shows the particle collection efficiency curves for three prototype CTD cells, with two types of challenge aerosols.

Calibration curves for the three geometries of the CTD cell are shown in FIG. 2. Tests were done with two types of challenge aerosols. Most tests were done using a challenge aerosol comprised of oleic acid, a nonhygroscopic oil. Some tests were done using a mixture of ammonium sulfate and oxalic aerosol, to form a hygroscopic aerosol. Results for a second prototype, the 10-jet, 0.28 mm orifice diameter, 7

L/min CTD (FIG. 1G) are shown by the triangular shaped symbols. For the nonhygroscopic aerosol, this CTD collected particles with diameters of 0.09 µm and larger with an efficiency of 50%, increasing to above 90% at 0.18 µm. For the hygroscopic test aerosol the collection efficiency is higher, with 50% efficiency at 0.06 µm, increasing to 90% at 0.11 µm. Results for a third, 9-jet prototype (FIG. 1F) is shown by the solid circular symbols. For the nonhygroscopic oleic acid aerosol, this cell had a 50% efficiency collection of particles at 0.07 µm, increasing to 90% at 0.12 µm. Data are also shown for a first prototype 1 L/min single-jet CTD (FIG. 1E) having a single, 0.37 mm diameter jet. This configuration was not as efficient as either the second or third prototypes.

The efficiency of thermal desorption and transfer from the CTD cell to the head of the chromatography column was evaluated using a standard solution comprised of a wide range of compounds including Dodecane, Hexadecane, Eicosane, Octacosane, Decanoic acid, Benzaldehyde, 4,4-Dimethoxybenzophenone, Acenaphthene, Chrysene, Levoglucosan, and Cholestane. Specifically, a comparison of the results obtained by introducing the standard with a microliter syringe through the GC injection port (traditional approach), to that obtained by thermal desorption of the same size standard aliquot from the CTD. For the CTD analysis, the standard aliquot was placed in a glass boat, the solvent was allowed to evaporate, and then the standard was thermally desorbed and transferred through the sampling valve directly onto the GC column.

For these tests the GC/MS was configured to incorporate a flame ionization detector (FID) in parallel to the mass spectrometer detector (MSD). The FID has the advantage of offering a more linear response with respect to the number of carbons, and of better stability over time. Multipoint calibration curves were generated for both the direct injection and thermal desorption modes.

Multipoint calibration curves for several representative compounds are shown in FIG. 3. Chrysene is a polycyclic aromatic hydrocarbon formed through combustion. Cholestane is one of the hopanes that serves as a biomarker for petroleum. Levoglucosan is a product of the combustion of cellulose, and is a powerful tracer for wood combustion. Eicosane is one of the many alkanes found in ambient particles. The FID and the MSD responses for sample introduction via thermal desorption from the CTD were compared to those obtained by sample introduction via the injection port, as is standardly done for filter extracts. We obtained excellent linear responses ($R^2 > 0.95$) and near zero intercepts for both injection modes for almost all compounds in the standard mixture, as listed in Table 1.

TABLE 1

Thermal Desorption Response to Laboratory Standards

| | CTD - MSD Response | | | | Flame Ionization Detector | |
|---|---|---|---|---|---|---|
| Compound | slope ($10^3$cts/ng) | intercept ($10^3$cts) | $R^2$ | Efficiency (CTD/Direct) | CTD (cts/fMC) | Direct (cts/fMC) |
| Acenaphthene | 795 | −146 | 0.976 | 1.00 | 6,071 | 6,120 |
| Hexadecane | 581 | −51 | 0.995 | 1.26 | 8,416 | 6,667 |
| Eicosane | 812 | 10 | 0.999 | 1.19 | 9,376 | 7,909 |
| Dimethoxybenzophenone | 153 | 4 | 0.999 | 0.97 | 4,218 | 4,342 |
| Chrysene | 2,192 | 172 | 0.991 | 1.11 | 6,228 | 5,638 |
| Octacosane | 838 | 182 | 0.999 | 1.41 | 8,454 | 5,944 |
| Cholestane | 1,090 | 13 | 0.994 | 1.38 | 12,419 | 9,019 |
| Levoglucosan | 151 | −128 | 0.981 | 2.59 | 2,057 | 577 |
| Decanoic acid | 83 | 32 | 0.816 | 0.53 | 2,045 | 3,691 |

Notes:
Simultaneous analysis by MSD and FID.
CTD refers to thermal desorption from CTD cell,
DIRECT refers to sample introduction with syringe through the injection port.
Efficiency calculated as relative CTD to DIRECT response at 10 ng as given by regression line.

Figure 4:
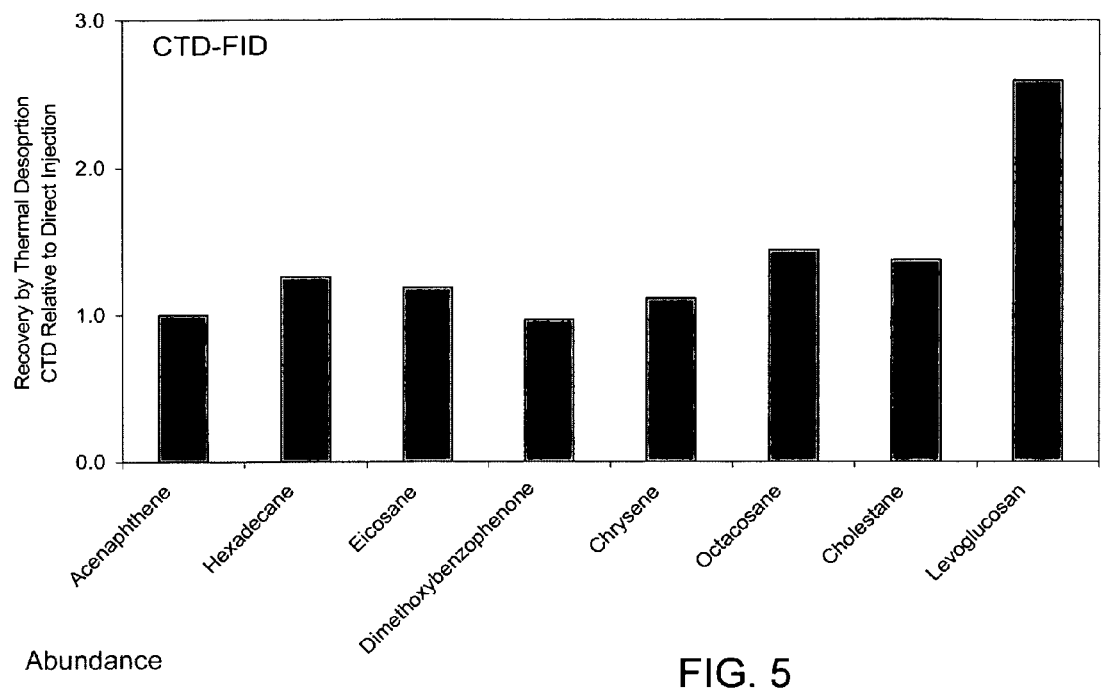
FIG. 4 is a bar graph comparing the recovery of compounds from thermal desorption from CTD cell to that from splitless introduction through the injection port, based on FID response.

Desorption and transfer efficiencies from the CTD relative to that for direct injection are displayed in FIG. 4. Results are calculated as the ratio of the CTD response to that of the direct injection for 10 ng of analyte, where individual response is calculated by the corresponding regression line from the multipoint calibration using data from the FID that is more stable over time than the MSD. As is evident, the transfer efficiency from the CTD is equivalent to that for direct injection for most compounds, and even better for levoglucosan, octacosane and cholestane. Neither approach shows good efficiency for levoglucosan or decanoic acid. For these compounds, the FID signal relative to the number of carbon atoms is much lower than that for the alkanes, indicating incomplete transfer of these compounds through the analytical system, regardless of the introduction technique. These compounds are known to be very difficult to transfer through gas chromatography systems, so they are generally derivatized prior to analysis.

Reproducibility for identifying and quantifying individual compounds in ambient aerosol samples was tested with ambient aerosol using off-line collection and subsequent analysis. This allowed collection of multiple samples in parallel for assessing measurement precision, and for assessing vapor adsorption artifact. Collection was done in Berkeley, Calif. located in the vicinity of an interstate highway. After collection, samples were transported to the GC/MS and the glass collection boats were inserted into the CTD cell mounted on the GC/MS for thermal desorption and analysis.

Figure 5:
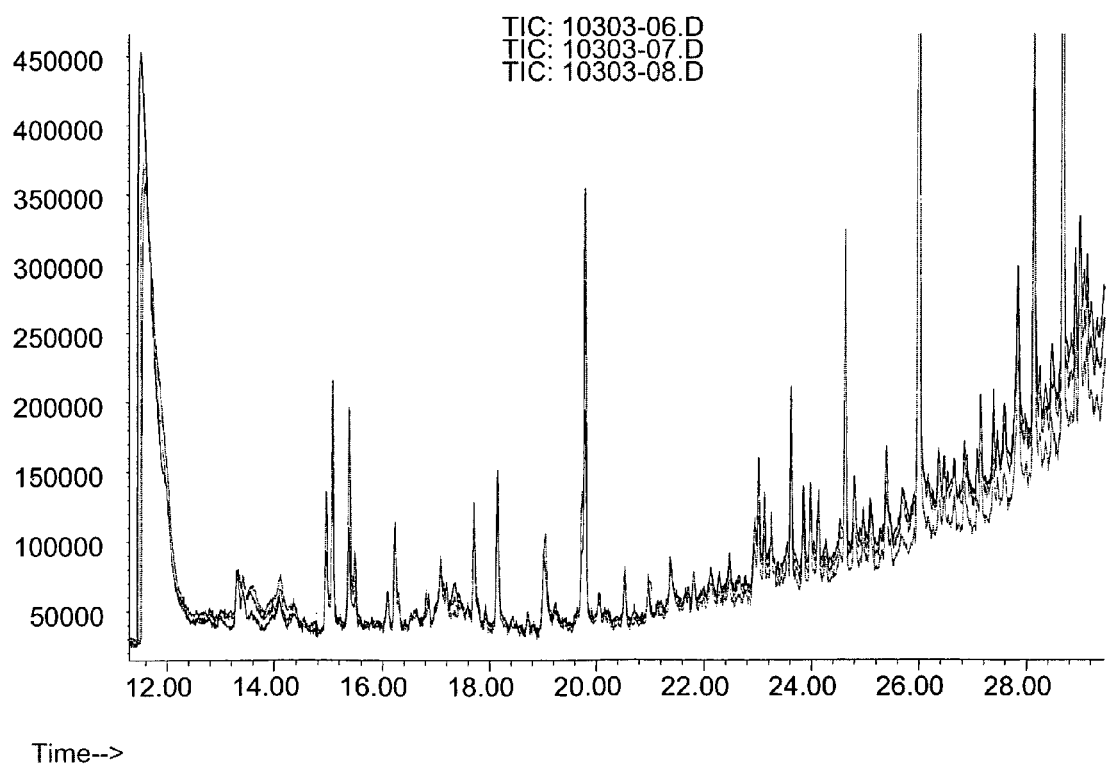
FIG. 5 is a graph comparing the chromatograms of three simultaneously collected ambient air aerosol samples (1 m 3 of air), analyzed by thermal desorption from a CTD cell.

Chromatograms from the analysis of three simultaneously collected samples are shown in FIG. 5. The reproducibility for quantifying individual compounds in ambient air samples can be assessed from these triplicate samples.

Figure 6:
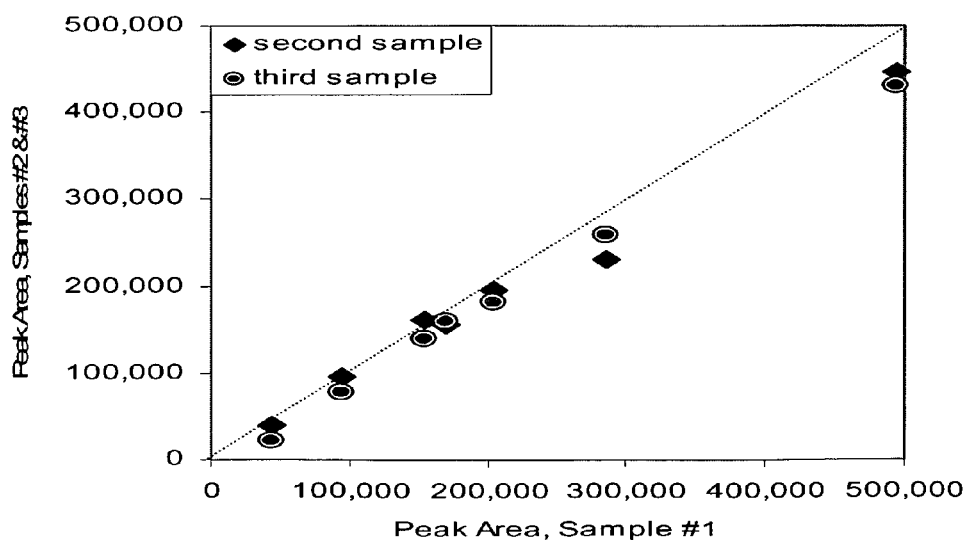
FIG. 6 is a plot comparing peak areas for analysis of independent, collocated samples of ambient air in Berkeley Calif.
Figure 3B:
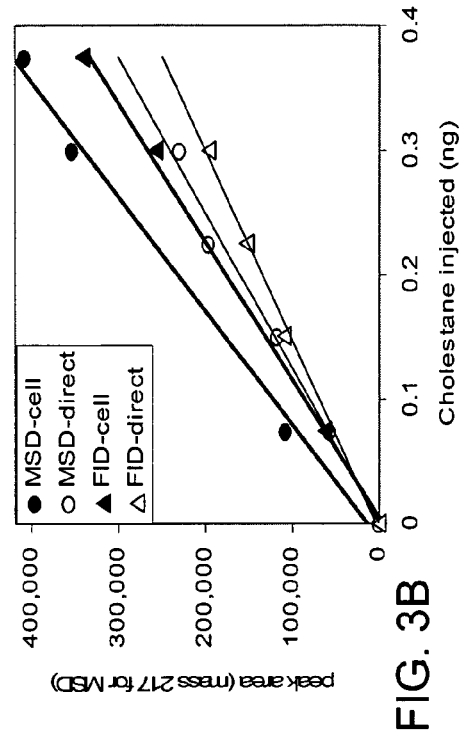
FIGS. 3A-3D show calibration curves for the CTD cell for four representative marker compounds, eicosane, cholestane, chrysene and levoglucosan, respectively, with comparison to the flame ionization detector (FID) response for direct injection.
Figure 3D:
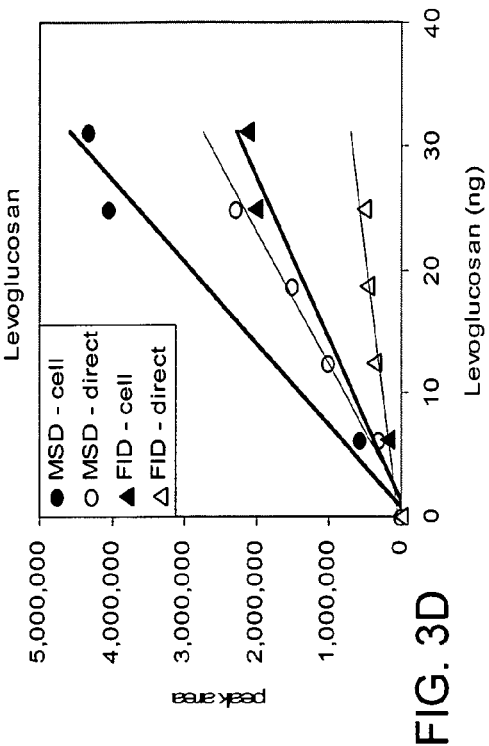
Figure 3A:
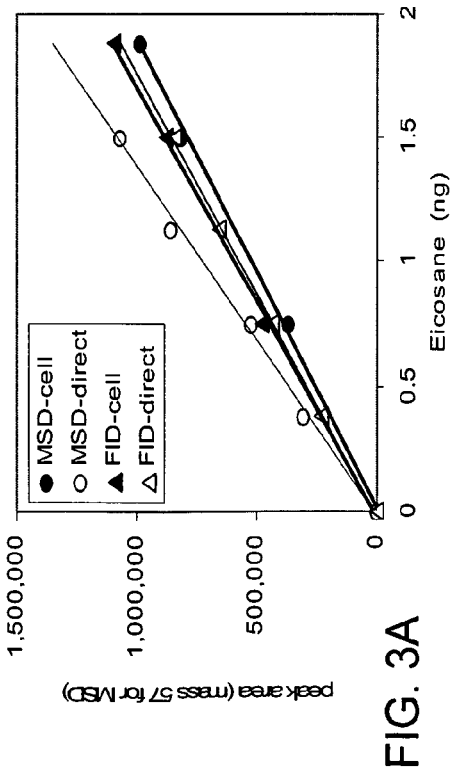
Figure 3C:
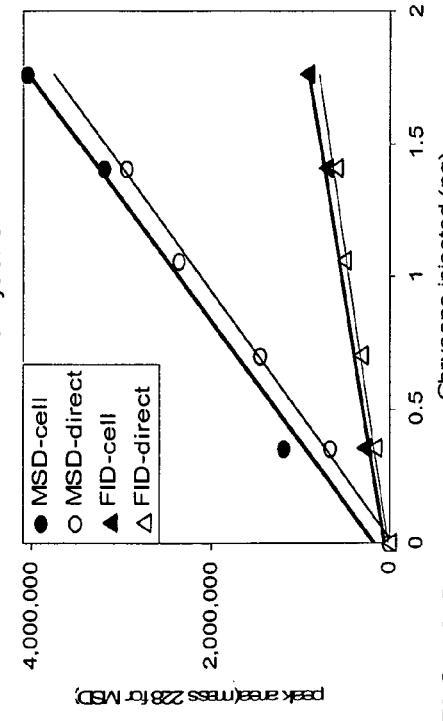

FIG. 6 shows a scatter plot of peak areas for a selection of compounds measured between the first of these triplicate samples and the other two. Some variability between the peak areas scales linearly indicating slight differences in sample size, but nearly identical relative responses. Standard deviations for measurements of individual compounds in the triplicate samples ranged from 0.04 to 0.33 for 11 selected representative compounds with a pooled std dev of 0.12, and reproducibility for the majority of these compounds was better than 10%.

Chromatograms from tests with a wood smoke sample and an ambient air sample are shown in FIGS. 7 and 8, respectively. FIG. 7 is a chromatogram of wood smoke sample analyzed directly from CTD cell via thermal desorption GC/MS (TIC: 35201-13.D, upper trace). Also shown are a system blank (TIC:35201-11.D, lowest trace) and a repeat analysis of the collection tube that had already been thermally desorbed (TIC35201-14.D, lower trace). The Figure shows repeat analysis of the sample, and a system blank, both of which exhibit very little background or sample residue, indicating excellent sample transfer during the initial thermal desorption and a clean system.

The samples were collected at a flow rate of 1 L/min over a period of 8 to 24 hours using a Silcosteel™ coated tube mounted inside a bored, stainless steel swage tee. After collection the sample cell was mounted directly onto the GC/MS. Samples were desorbed using a slow temperature ramp to 300° C. over 5 minutes, then transferred directly to the GC column through a valve and tubing held at 150-200 C. A strong signal and reasonable separation was obtained using a sample volume that can easily be obtained within a one-hour collection period. In both cases the signal is much larger than from the system blanks, which were extremely clean. For the wood smoke sample a repeat analysis of the collection tube that had already been thermally desorbed showed very little residual material, suggesting that we had excellent sample transfer during the initial thermal desorption.

Figure 9A:
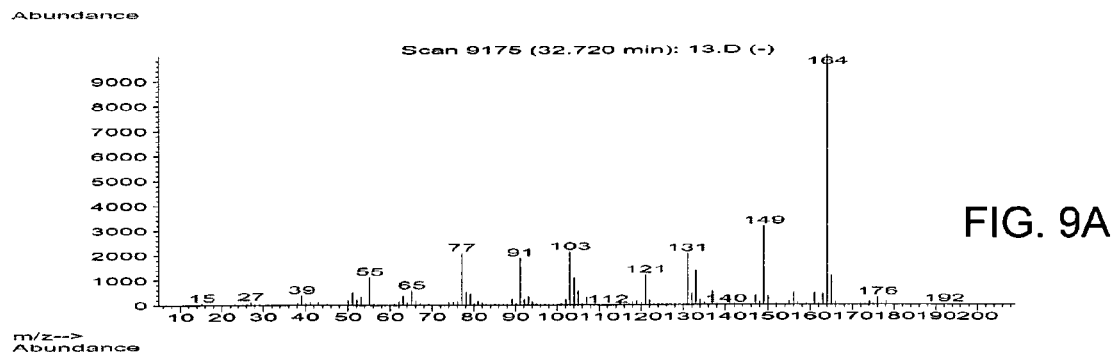
FIGS. 9A-9D illustrate comparisons of the mass spectra from two of the observed compounds from the woodsmoke sample (FIGS. 9A and 9C) to compounds from the NIST 1998 mass spectral database (FIGS. 9B and 9D), where
Figure 9B:
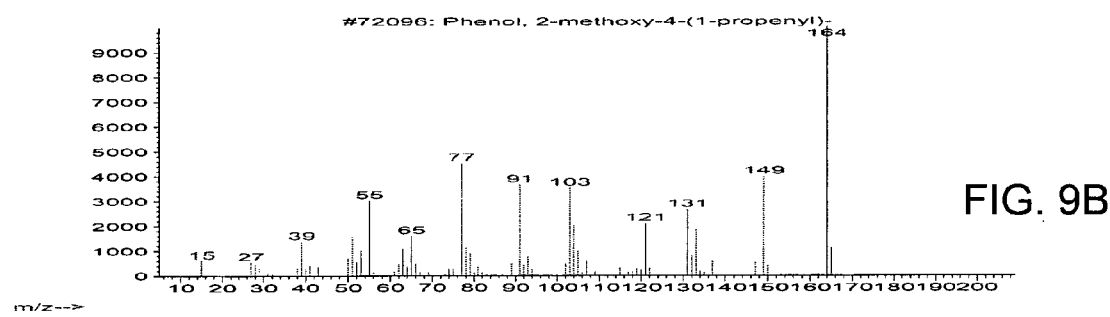
Figure 9C:
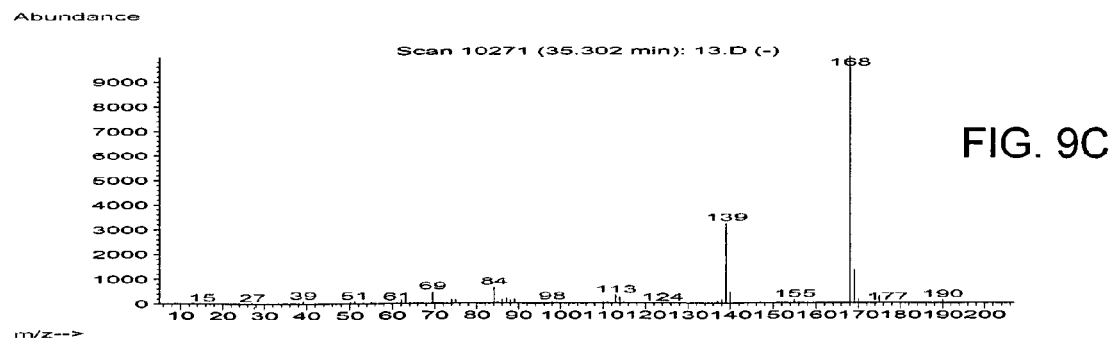
Figure 9D:
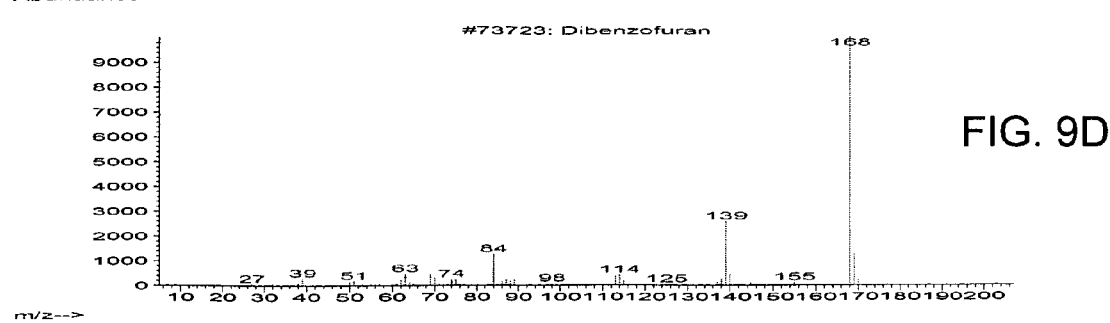

FIGS. 9A-9D show examples of measured spectra with comparison to the National Institute of Standards and Technology (NIST) reference spectra. The Figures compare the mass spectra from two of the observed compounds (FIGS. 9A and 9C) from the woodsmoke sample to compounds from the NIST 1998 mass spectral database (FIGS. 9B and 9D). FIGS. 9A and 9C show the observed mass spectrum, and 9B and 9D shows the library match and identification for each compound respectively. The compounds identified in the samples are typical of the suite of compounds previously identified in wood smoke and ambient air samples by filter extraction GC/MS techniques (e.g. Rogge et al., 1998) including several important classes of compounds which could serve as source markers including n-alkanes, n-alkenes, n-alkanalys, n-alkanoic acids, methoxylated phenols, naphthalenes and substituted benzenes and benzaldehydes.

Figure 10:
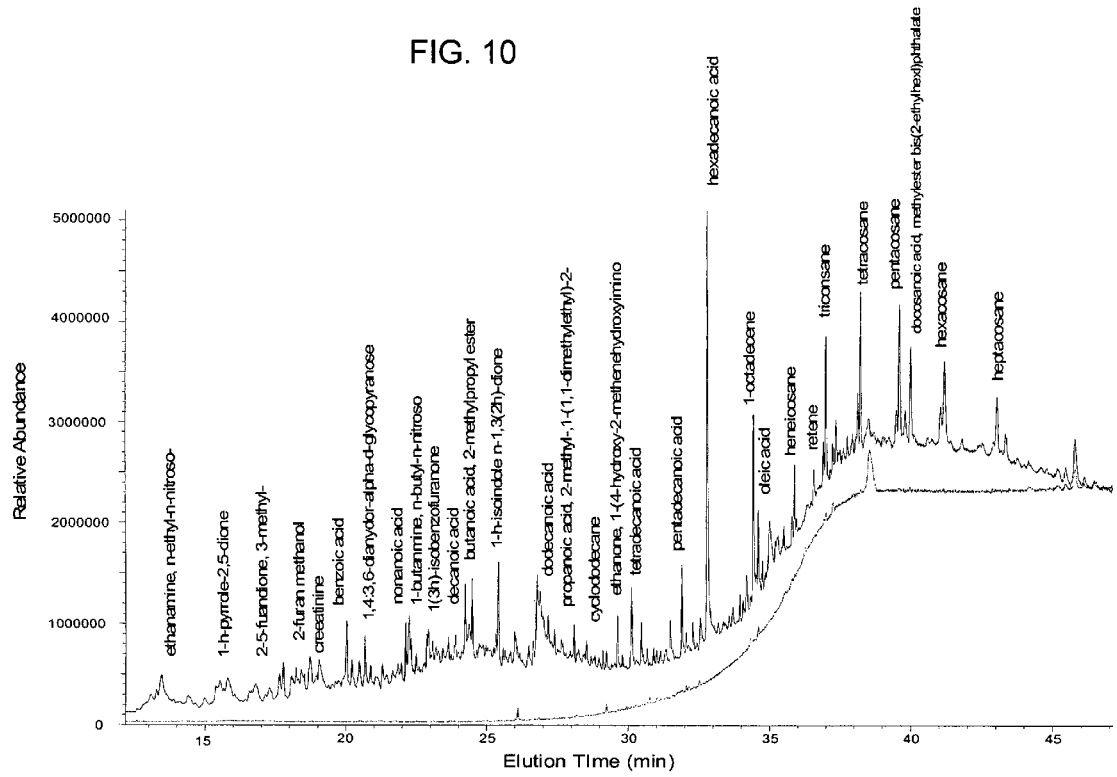
FIG. 10 is a chromatogram of an ambient air sample from Berkeley, Calif., collected and analyzed by CTD cell coupled to the GC/MS. Compounds labeled as identified by the NIST mass spectra database.
Figure 11:
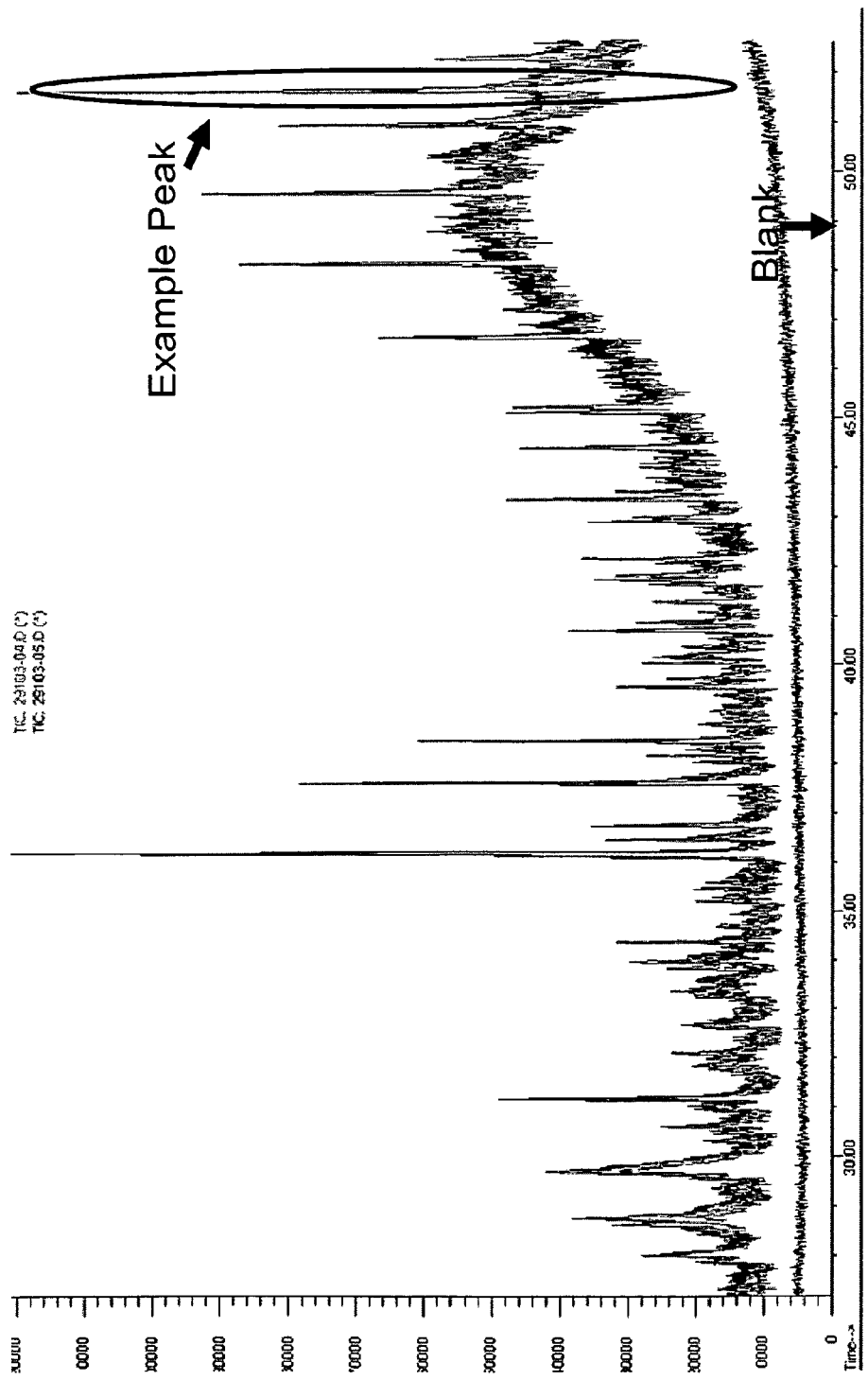
FIG. 11 shows the chromatograms from four consecutive ambient aerosol samples collected with the automated Aerosol GC/MS/FID, with comparison to a blank. Mass spectra from the example peak are given in FIG. 12.
Figure 12:
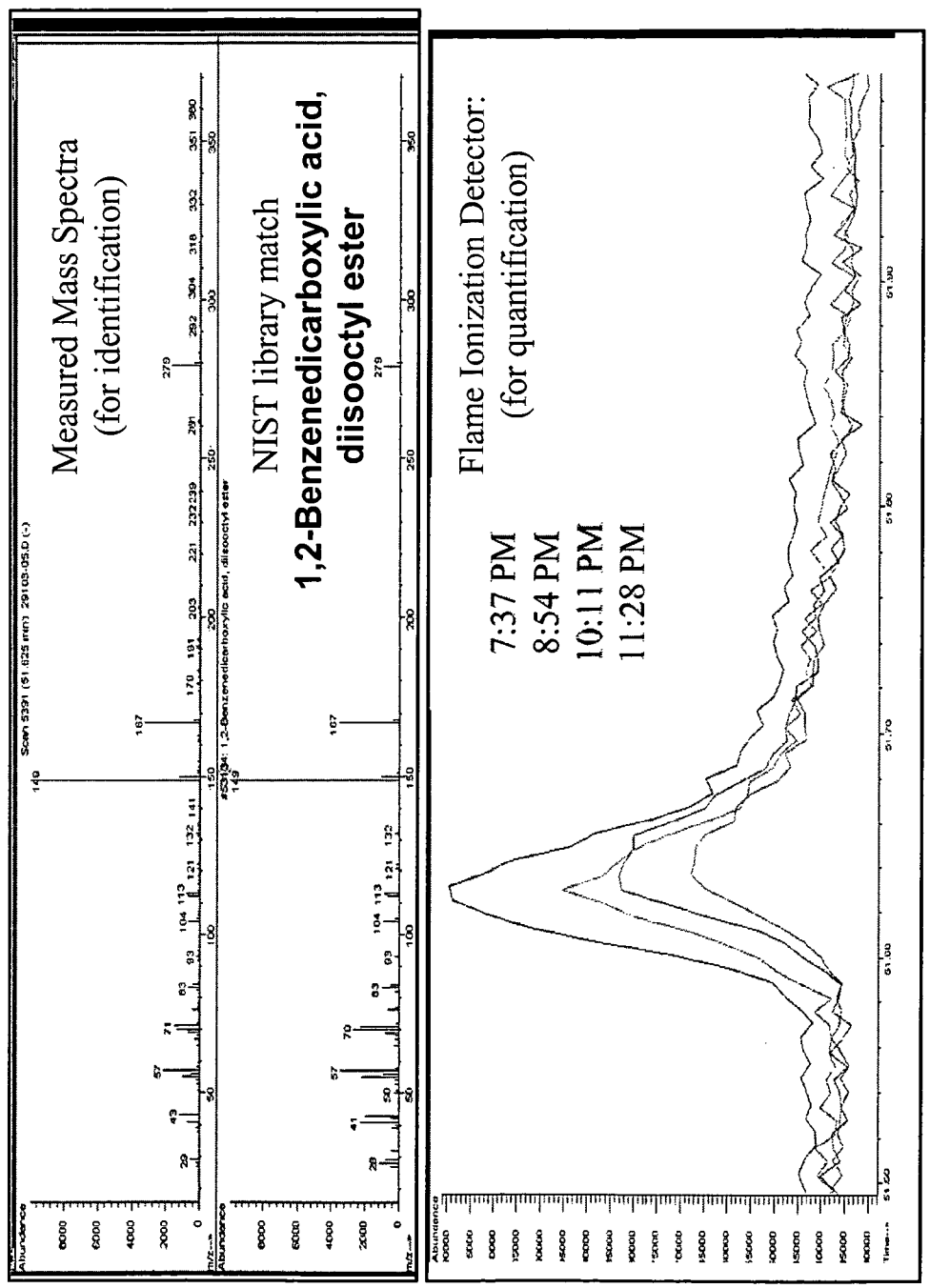
FIG. 12 is an expansion of the FID signal from the chromatograms of FIG. 11 showing a common peak at 51.65 minutes. The simultaneous mass spectrometry signal provides identification of the peak, based on the NIST database, as 1,2 benzenedicarboxylic acid diisoocty ester.

A chromatogram from an ambient air sample collected with a glass CTD cell is shown in FIG. 10. many compounds are clearly resolved above the background. Some of those identified by the NIST mass spectra database are labeled. Consecutive samples collected with a fully automated system are shown in FIG. 11. These data were obtained with a multijet collector operated at a sample flow rate of 7 L/min. Collection time for each sample is approximately 45 minutes. FIG. 12 shows the change in one of the peaks, identified from the NIST database as 1,2 benzenedicarboxylic acid diisooctyl ester.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. A method for in-situ, chemical analysis of airborne particles, comprising the in-situ steps of:
    collecting an air stream from ambient air into a sampling and analysis system including a humidifier coupled via a first isolation element to a collection cell, the collection cell selectively coupled to a gas chromatography column isolated from the collection cell during said collecting by a second isolation element, the ambient air collected at a sampling inlet and passed to the humidifier;
    humidifying the sample air stream using the humidifier,
    passing the sample air stream from the humidifier through to the particle collection cell;
    depositing particulate material from the sample air stream in the collection cell;
    isolating the collection cell from the sampling inlet using the first isolation element;
    opening the second isolation element and directing carrier gas through the cell and through the gas chromatography column;
    thermally desorbing the particulate material in the collection cell into said carrier gas by heating the collection cell to provide desorbed particulate material;
    transporting the desorbed particulate material in the carrier gas through a heated transport line directly onto a head of the gas chromatography column;
    re-depositing the particulate material on the head of the chromatography column, the temperature of the chromatography column being controlled to less than or equal to 50° C.;
    separating the particulate material constituents using said gas chromatography column; and
    analyzing the constituents of the particulate material as they evolve from the gas chromatography column.

2. The method of claim 1 the step of depositing the particulate material includes collecting by means of impaction.

3. The method of claim 2 wherein the step of humidifying further including the step of humidifying the particle sample stream to a range of about 65% prior to collection.

4. The method of claim 1 wherein the step of thermally desorbing includes heating the collected particulate material to approximately 300° C. over a period of 3 to 10 minutes.

5. The method of claim 1 wherein the step of thermally desorbing is done into a carrier gas of Helium.

6. The method of claim 1 wherein the step of transporting comprises transporting the carrier gas and desorbed material directly into the gas chromatograph.

7. The method of claim 1 wherein the step of analyzing comprises holding the chromatography column at a temperature between 20 and 50° C. during desorption.

8. The method of claim 7 wherein the step of transporting includes heating the particulate material.

9. The method of claim 1 further including venting material desorbing below 80 Degrees C., such that only that material which desorbs within a selected temperature range is directed to the analysis step.

10. The method of claim 1 further including isolating between the chromatography column and the collection cell using a heated valve.

11. The method of claim 1 wherein the analyzing step includes analyzing using a mass spectrometer.

12. The method of claim 1 wherein the analyzing step includes analyzing using a flame ionization detector.

13. The method of claim 1 wherein the analyzing step includes analyzing using a flame ionization detector and a mass spectrometer operated in parallel.

14. The method of claim 1 wherein the analysis step for a first sample occurs during the step of collecting a second sample.

15. The method of claim 1 further including establishing background signals by collecting filtered air samples.

16. The method of claim 1 further including a step following said isolating step of passing a carrier gas through the collection cell and simultaneously heating the cell to an intermediate temperature to thermally desorb and discard volatile components.

* * * * *